ced Patent [19] [11] 4,003,914
Ramuz [45] Jan. 18, 1977

[54] SULPHUR CONTAINING DERIVATIVES

[75] Inventor: Henri Ramuz, Birsfelden, Switzerland

[73] Assignee: Hoffmann-La Roche Inc., Nutley, N.J.

[22] Filed: Dec. 16, 1974

[21] Appl. No.: 532,990

[30] Foreign Application Priority Data
Dec. 21, 1973 Switzerland .................. 18030/73
Nov. 16, 1974 Switzerland .................. 15248/74

[52] U.S. Cl. ................. 260/327 M; 260/329 HS;
260/332.3 R; 260/332.3 P; 260/332.3 C;
260/332.5; 260/340.7; 260/340.9; 260/465 E;
260/468 E; 260/471 R; 260/488 CD; 260/518
A; 260/518 R; 260/556 C; 260/556 AR;
260/558 A; 260/562 R; 260/570.5 R;
260/570.5 C; 260/570.5 P; 424/275; 424/277
[51] Int. Cl.$^2$ ..................................... C07D 339/06
[58] Field of Search ..................... 260/327 M

[56] References Cited
UNITED STATES PATENTS
3,766,209 10/1973 Emmick ................... 260/327 M FOREIGN PATENTS OR APPLICATIONS
1,154,810 9/1963 Germany
2,000,435 10/1971 Germany
43/13841 5/1967 Japan Primary Examiner—Henry R. Joles
Assistant Examiner—C. Jaisle
Attorney, Agent, or Firm—Samuel L. Welt; George M. Gould

[57] ABSTRACT

A novel class of dithiane and disulfone compound is described. These compounds are pharmaceutically active as coronary dilating agents and thus can be used therapeutically in cases of insufficient cardiac blood supply, i.e., in the treatment of angina pectoris. A preferred compound is N-(3,4-dimethoxyphenethyl)-2-(3,4-dimethoxyphenyl)-N-methyl-m-dithiane-2-propylamine-1,1-3,3-tetraoxide.

15 Claims, No Drawings

SULPHUR CONTAINING DERIVATIVES

Prior Art

German Auslegeschrift No. 1,154,810 (Derwent 9161) Knoll A. G.
German Auslegeschrift No. 2,000,435 (Derwent 399675) Kali-Chemie A. G.

Description of the Invention

The present invention relates to sulphur-containing derivatives. More particularly, the invention is concerned with sulphur-containing derivatives, a process for the manufacture thereof and pharmaceutical preparations containing same.

The sulphur-containing derivatives provided by the present invention are compounds of the general formula

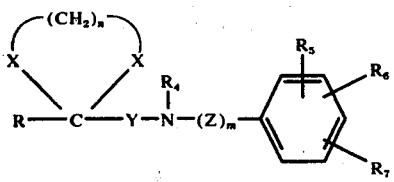

(I)

, wherein R is a group of the formula

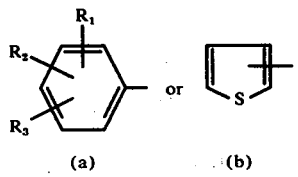

in which $R_1$, $R_2$ and $R_3$ each independently is hydrogen, halogen, lower alkyl, lower alkoxy, aryl-(lower alkoxy), aryloxy, phenyl, nitro, amino, lower alkylthio, trifluoromethyl, hydroxy, cyano, di(lower alkyl)amino, lower alkanoylamino, carboxyl, lower alkoxycarbonyl, lower alkylsulphonyl, hydroxymethyl, lower alkanoyloxy, amido, lower alkanoyl, sulphamoyl, mono(lower alkyl)-sulphamoyl, di(lower alkyl)sulphamoyl, aminocarbonyloxy, mono(lower alkyl)aminocarbonyloxy, di(lower alkyl)aminocarbonyloxy or (lower alkylamino)-(lower alkyl) or two adjacent $R_1$, $R_2$ and $R_3$ symbols together represent a methylenedioxy, ethylenedioxy or butadien-1,3-ylene-1,4 group; R is hydrogen or lower alkyl, $R_5$, $R_6$ and $R_7$ each independently is hydrogen, halogen, lower alkyl, lower alkoxy, hydroxy or benzyloxy or two adjacent $R_5$, $R_6$ and $R_7$ symbols together are methylenedioxy or ethylenedioxy; X is a sulphur atom, SO or $SO_2$; Y is a straight-chain or branched-chain, aliphatic group which may be substituted with hydroxy, said aliphatic group containing 2-8 carbon atoms, of which 2-4 carbon atoms are present in the chain, and Z is a straight-chain or branched-chain, aliphatic group which may be substituted with hydroxy, said aliphatic group containing 1-8 carbon atoms, of which 1-4 carbon atoms are present in the chain, m stands for zero or 1 and n stands for 2 or 3, and acid addition salts thereof.

As used in this description and in the accompanying claims, the term "lower alkyl" means straight-chain or branched-chain alkyl groups containing 1-6 carbon atoms (e.g. methyl, ethyl, n-propyl, isopropyl, n-butyl, isobutyl, tert. butyl, amyl, hexyl and the like). The term "lower alkoxy" means lower alkyl ether groups in which the "lower alkyl" moiety has the aforementioned significance. The term "halogen" means fluorine, chlorine, bromine and iodine. The term "lower alkanoyl" means alkanoyl groups containing up to 6 carbon atoms (e.g. formyl, acetyl, propionyl, butyryl and the like). The term "aryl" means unsubstituted or substituted phenyl, the substituent(s) being selected from halogen, lower alkyl, lower alkoxy, nitro and amino. The term "leaving atom or group" used hereinafter means known atoms and groups such as, for example, halogen, preferably bromine or chlorine, arylsulphonyloxy such as tosyloxy, alkylsulphonyloxy such as mesyloxy or an epoxy group and the like.

Preferred compounds of formula I are, for example, those of the following general formula

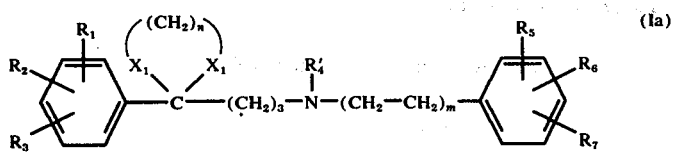

(Ia)

, wherein $R_1$-$R_7$ and m are as above, $R'_4$ is a methyl or ethyl and $X_1$ is a sulphur atom or $SO_2$.

Preferred compounds falling within formula Ia are those in which one of the symbols $R_1$, $R_2$ and $R_3$ is hydrogen and the other symbols each is lower alkoxy, especially methoxy, or together are a butadien-1,3-ylene-1,4-group and those in which two of the symbols $R_1$, $R_2$ and $R_3$ each is hydrogen and the third symbol is nitro and one of the symbols $R_5$, $R_6$ and $R_7$ is hydrogen and the other two symbols each is lower alkoxy, especially methoxy. An especially preferred compound is N-(3,4-dimethoxyphenethyl)-2-(3,4-dimethoxyphenyl)-N-methyl-m-dithiane-2-propylamine-1,1,3,3-tetraoxide.

The sulphur-containing derivatives aforesaid (i.e. the compounds of formula I and their acid addition salts) are conveniently prepared by a. reacting a compound of the general formula

(II)

, wherein R, X and n are as above, with a compound of the general formula

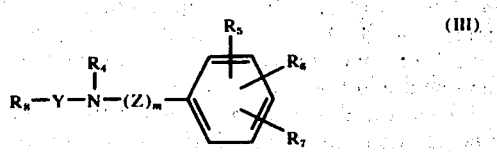

wherein $R_4$-$R_7$, Y, Z and m are as above and $R_8$ is a leaving atom or group, or b. reacting a compound of the general formula

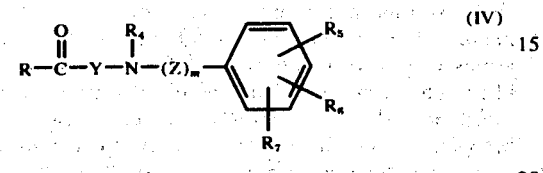

wherein R, $R_4$-$R_7$, Y, Z and m are as above, with a compound of the general formula

wherein n is as above, or c. reacting a compound of the general formula

wherein R, $R_8$, X, Y and n are as above, with a compound of the general formula

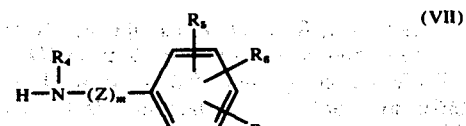

wherein $R_4$-$R_7$, Z and m are as above, or d. reacting a compound of the general formula

wherein R and $R_8$ are as above, with a compound of the general formula

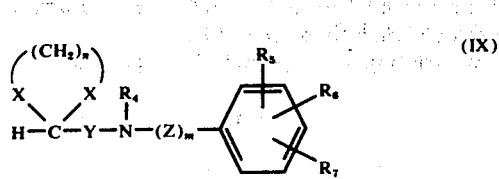

wherein $R_4$-$R_7$, X, Y, Z, n and m are as above, or e. reacting a compound of the general formula

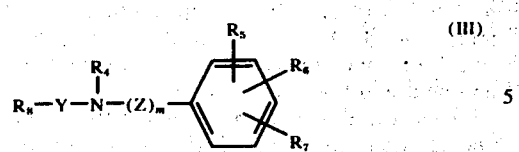

wherein R, $R_4$, X, Y and n are as above, with a compound of the general formula

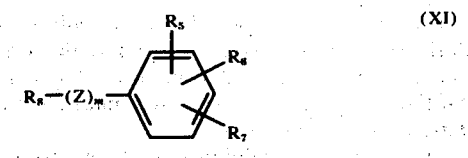

wherein $R_5$, $R_8$Z and m are as above, or f. reducing the carbonyl group or the group denoted by A in a compound of the general formula

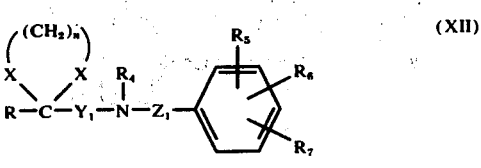

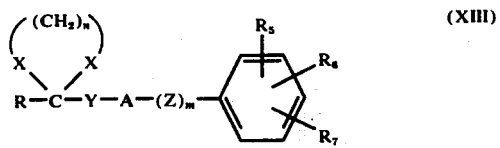

wherein R, $R_4$-$R_7$, X, Y, Z, m and n are as above, $Y_1$ and $Z_1$ each respectively is a group corresponding to Y or Z containing a carbonyl group and A is the group

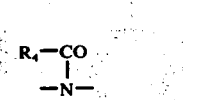

in which $R_4$ is as above, optional steps which may be carried out on the products of the above processes includes: oxidizing a compound of formula I in which X is a sulphur atom to a compound for formula I in which X is SO or $SO_2$; N-(lower alkylating) a compound of formula I in which $R_4$ is hydrogen; converting a lower alkoxy group or an aryl-(lower alkoxy) group into a hydroxy group; reducing a nitro group to an amino group; saponifying a cyano group to a carboxyl group; esterifying or amidating or reducing a carboxyl group; etherifying or esterifying or carbamoylating a hydroxy group; mono(lower alkylating) or di(lower alkylating) an amino group; oxidizing an alkylthio group to an alkylsulphonyl group and; converting a base obtained into an acid addition salt.

The reaction of a compound of formula II with a compound of formula III according to embodiment a) of the process can be carried out in a manner known per se. The reaction is expediently carried out in an organic solvent which is inert under the reaction conditions and at a temperature between about $-80°$ C and the reflux temperature of the reaction mixture, preferably between about $0°$ C and about $50°$ C and especially at about room temperature. Suitable solvents include ethers (e.g. diethyl ether, tetrahydrofuran, dioxane or the like), aromatic hydrocarbons (e.g. benzene, toluene, xylene etc), dimethylformamide, dimethyl sulphoxide or the like. The reaction is carried out in the presence of a strong base such as butyl lithium, a Grignard compound, sodium or sodium hydride. An especially strong base such as butyl lithium or a Grignard compound is expediently used when X is a sulphur atom.

The starting materials of formulae II and III are partly known and partly novel. Those which are novel also form part of the present invention. The novel compounds can be prepared in a manner known per se, namely in a manner analogous to the preparation of the known compounds.

Those compounds of formula II in which X represents a sulphur atom can be prepared, for example, by reacting an aldehyde of the general formula

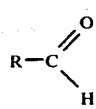

, wherein R is as above,
with ethanedithiol or propanedithiol. The reaction is conveniently carried out in an inert organic solvent (e.g. chloroform) and at a temperature below room temperature.

Those compounds of formula II in which X represents SO or $SO_2$ can be prepared by oxidizing a corresponding compound of formula II in which X represents a sulphur atom. The oxidation can be conveniently carried out in a suitable solvent using a peracid such as peracetic acid, perphthalic acid, m-chloroperbenzoic acid or the like. Peracetic acid can, for example, be formed in situ from glacial acetic acid and hydrogen peroxide.

The reaction of a compound of formula IV with a compound of formula V according to embodiment b) of the process can be carried out in a manner known per se. The reaction is expediently carried out in an organic solvent which is inert under the reaction conditions, preferably in a polar solvent such as halogenated hydrocarbon (e.g. chloroform, methylene chloride or the like) or ethyleneglycol dimethyl ether, etc. The reaction is also expediently carried out in the presence of a water-cleaving agent (e.g. sulphuric acid, a hydrohalic acid, phosphoric acid, etc) and at a temperature between about 0° C and the reflux temperature of the reaction mixture, preferably at room temperature.

The starting materials of formula V are known and can be prepared in a known manner.

The starting materials of formula IV are novel and also form part of the present invention.

The starting materials of formula IV can be prepared, for example, by reacting a compound of the general formula

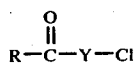 (XIVa)

with a compound of the general formula

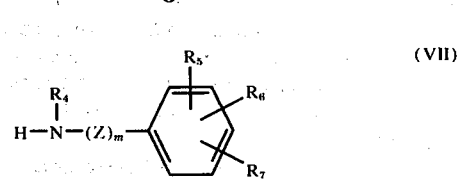

wherein $R_4$-$R_7$, Z and m are as above.

The reaction is expediently carried out in the presence of an acid-binding agent such as a tertiary amine (e.g. N-ethyl-N,N-diisopropylamine) which simultaneously serves as the solvent. The reaction is also expediently carried out at an elevated temperature, preferably at a temperature up to about 130° C, depending on the boiling point of the solvent.

The compounds of formula XIVa are partly known and partly novel. The novel compounds can be prepared in a manner known per se, namely in a manner analogous to the preparation of the known compounds. The compounds of formula VII are known.

The reaction of a compound of formula VI with a compound of formula VII in accordance with embodiment c) of the process can be carried out in a manner known per se. The reaction is expediently carried out in an organic solvent which is inert under the reaction conditions, such as an ether (e.g. dibutyl ether, dioxane or tetrahydrofuran), an alkanol (e.g. ethanol or propanol), an aromatic hydrocarbon (e.g. benzene, toluene or zylene), acetonitrile, dimethylformamide, dimethyl sulphoxide or the like. The reaction can be carried out at a temperature between about room temperature and the reflux temperature of the reaction mixture. The reaction is preferably carried out at the reflux temperature. The reaction is expediently carried out in the presence of a base (e.g. a tertiary amine such as trimethylamine, N-ethyl-N,N-diisopropylamine, N,N-dimethylaniline or the like) in the case where acid is cleaved during the reaction.

The starting materials of formula VII are known. The starting materials of formula VI, however, are novel and also form part of the present invention. The starting materials of formula VI can be prepared, for example, by reacting a compound of the general formula

 (XIV)

, wherein R, $R_8$ and Y are as above,
with a compound of the general formula

 (V)

, wherein n is as above, and, if desired, converting a thus obtained compound of the formula VI in which X represents a sulphur atom into a compound of formula VI in which X represents SO or $SO_2$ by oxidation.

The reaction of a compound of formula XIV with a compound of formula V can be carried out in a manner known per se. The reaction is expediently carried out in an organic solvent which is inert under the reaction conditions, preferably in a polar solvent such as a halogenated hydrocarbon (e.g. chloroform, methylene chloride or the like) or ethyleneglycol dimethyl ether, etc. The reaction is also expediently carried out in the presence of a water-cleaving agent (e.g. sulphuric acid, a hydrohalic acid, phosphoric acid, etc) and at a temperature between about 0° C and the reflux temperature of the reaction mixture, preferably at room temperature.

The conversion of a thus obtained compound of formula VI in which X represents a sulphur atom into a compound of formula VI in which X represents SO or $SO_2$ can be carried out in a manner known per se; for example, by oxidation with a peracid such as, for example, peracetic acid, perphthalic acid, m-chloroperbenzoic acid and the like. Peracetic acid can, for example, be formed in situ from glacial acetic acid and hydrogen peroxide.

The reaction of a compound of formula VIII with a compound of formula IX in accordance with embodiment d) of the process can be carried out in a manner known per se. The reaction is expediently carried out in an organic solvent which is inert under the reaction conditions, such as an ether (e.g. tetrahydrofuran, dioxane, diethyleneglycol diethyl ether or the like), acetonitrile, dimethylformamide etc. The reaction is carried out at a temperature between about room temperature and the reflux temperature of the reaction mixture, preferably at the reflux temperature. The reaction is carried out in the presence of a strong base such as butyl lithium, a Grignard compound, sodium, sodium hydride and the like. An especially strong base such as butyl lithium or a Grignard compound is expediently used when X represents a sulphur atom.

The starting materials of formula VIII are known. The starting materials of formula IX, however, are novel and also form part of the present invention. The starting materials of formula IX can be prepared, for example, by reacting a compound of the general formula

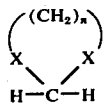
(XV)

, wherein X and n are as above,
with a compound of formula III hereinbefore. This reaction can be carried out in a manner known per se. The reaction is expediently carried out in an organic solvent which is inert under the reaction conditions and at a temperature between about −80° C and the reflux temperature of the reaction mixture, preferably between about 0° C and about 50° C and especially at about room temperature. As solvents, there may be mentioned ethers (e.g. diethyl ether, tetrahydrofuran, dioxane or the like), aromatic hydrocarbons (e.g. benzene, toluene, zylene, etc), dimethylformamide, dimethyl sulphoxide or the like. The reaction is carried out in the presence of a strong base such as butyl lithium, a Grignard compound, sodium, sodium hydride or the like. An especially strong base such as butyl lithium or a Grignard compound is expediently used when X represents a sulpher atom.

The compounds of formula XV are known. The compounds of formula III are partly novel and partly known. The novel compounds of formula III can be prepared in a manner known per se, namely in a manner analogous to the preparation of the known compounds.

The reaction of a compound of formula X with a compound of formula XI in accordance with embodiment e) of the process can be carried out in a manner known per se. The reaction is expediently carried out in an organic solvent which is inert under the reaction conditions, such as an ether (e.g. dibutyl ether, dioxane or tetrahydrofuran), an alkanol (e.g. ethanol or propanol), an aromatic hydrocarbon (e.g. benzene, toluene or xylene), acetonitrile, dimethylformamide, dimethyl sulphoxide or the like. The reaction can be carried out at a temperature between about room temperature and the reflux temperature of the reaction mixture, preferably at the reflux temperature. The reaction is expediently carried out in the presence of a base (e.g. a tertiary amine such as triethylamine, N-ethyl-N,N-diisopropylamine, N,N-dimethylaniline or the like) in the case where acid is cleaved during the reaction.

The starting materials of formula XI are known. The starting materials of formula X, however, are novel and also form part of the present invention. The starting materials of formula X can be prepared, for example, by reacting a compound of the general formula

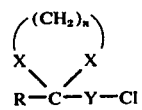
(VIa)

, wherein R, X, Y and n are as above,
with an amine of the general formula $$R_4-NH_2$$
(XVI)

wherein $R_4$ is as above.

Since, in carrying out this reaction, hydrogen chloride is cleaved off, the reaction is expediently carried out in the presence of a base or using an excess of the amine of formula XVI. Furthermore, the reaction can be carried out in a manner analogous to that described earlier in connection with the reaction of a compound of formula VI with a compound of formula VII.

The compounds of formula XVI are known. The compounds of formula VIa, which are partly novel, can be prepared in a manner analogous to the preparation of the compounds of formula VI.

The reduction of a carbonyl group A in a compound of formula XII or XIII in accordance with embodiment f) of the process can be carried out in a manner known per se.

Thus, an amide of formula XII or XIII (i.e. a compound in which the carbonyl group is bonded directly to the nitrogen atom) can be reduced by treatment with a metal hydride (e.g. lithium aluminium hydride or diisobutyl aluminium hydride) or with diborane or the like. This reduction is expediently carried out in an organic solvent which is inert under the reduction conditions (e.g. an ether such as diethyl ether, tetrahydrofuran etc. or diglyme) and at a temperature between about 0° C and the reflux temperature of the reduction mixture, preferably at about room temperature.

The reduction of other carbonyl groups (i.e. those which are not bonded directly to the nitrogen atom) can also be carried out in a manner known per se. In particular, the reduction can be carried out in such a manner that it either leads to a hydroxymethylene group, which can then be further reduced to a methylene group, or leads directly to a methylene group.

The reduction to a hydroxymethylene group can be carried out by treatment with a complex metal hydride such as an alkali metal hydride or an alkali metal borohydride.

The further reduction of a hydroxymethylene group to a methylene group can be carried out in a manner known per se, especially by conversion into a corresponding sulphonic acid ester or into a halide and reduction thereof with a complex metal hydride. These reductions can be carried out in a manner analogous to the reduction of carbonyl groups described hereinbefore.

The direct reduction of a carbonyl group to a methylene group can be carried out by means of a Wolff-Kishner reaction in a manner known per se, namely by reaction of the ketone with hydrazine to give the corresponding hydrazone and decomposition of the hydrazone under basic conditions.

The starting materials of formulae XII and XIII are novel and also form part of the present invention.

Amides of formula XII can be prepared, for example, by reacting an acid of the general formula

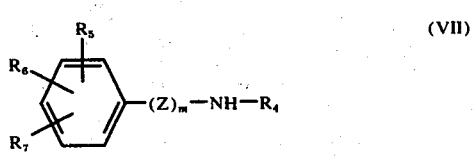
(VII)

, wherein R, Y, X and n are as above,
with an amine of the general formula

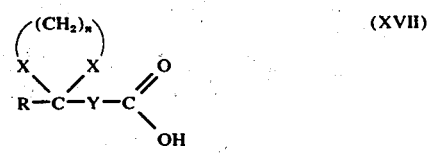
(XVII)

wherein $R_4$–$R_7$, Z and m are as above. The reaction can be expediently carried out in the presence of a tertiary amine (e.g. triethylamine) and a halocarboxylic acid ester (e.g. chloroformic acid isobutyl ester) (mixed anhydride method) in an inert organic solvent (e.g. tetrahydrofuran) and at a temperature of from about 0° C to about 30° C.

The acids of formula XVII can be prepared in a manner analogous to that described hereinbefore for the preparation of compounds of formula VI starting from compounds of the general formula

(XVIII)

wherein R is as above. The compounds of formula XVIII are known.

The ketones of formula XII can be prepared in a manner known per se; for example, by oxidizing a corresponding alcohol. The oxidation can be carried out, for example, using chromium trioxide/pyridine in pyridine at a temperature of from about −20° C to about room temperature, preferably at about 0° C.

The amides of formula XIII can be prepared in a manner known per se; for example, by acylating a compound of formula I in which $R_4$ is hydrogen. The acylation can be carried out, for example, using a halide of a lower carboxylic acid in a tirtiary amine (e.g. pyridine) at a temperature of from about 0° C to about 30° C, preferably at about room temperature.

The conversion of a compound of formula I in which X represents a sulphur atom into a compound of formula I in which X represents SO or $SO_2$ can be carried out by oxidation, in a suitable solvent, with a peracid such as peracetic acid, perphthialic acid, m-chloroperbenzoic acid or the like. Peracetic acid can, for example, be formed in situ from glacial acetic acid and hydrogen peroxide.

Compounds of formula I in which $R_4$ is hydrogen can be N-(lower alkylated) in a manner known per se; for example, using a lower alkyl halide. In this procedure, the particular compound of formula I is expediently reacted directly with the alkyl halide at a low temperature.

The conversion of a lower alkoxy group or an aryl-(lower alkoxy) group into a hydroxy group can be carried out in a manner known per se; for example, by heating with a concentrated hydrohalic acid, especially constant boiling hydrobromic acid.

the reduction of a nitro group to an amino group can be carried out chemically or catalytically in a manner known per se; for example, using tin/hydrochloric acid or hydrogen in the presence of a noble metal catalyst. The hydrogenation is preferably carried out in an alkanol, especially ethanol, in the presence of palladium/carbon or platinum oxide under normal pressure at room temperature.

The saponification of a cyano group can be carried out using an acid or a base in a manner known per se.

The esterification or amidation of a carboxyl group can be carried out in a manner known per se; for example, by treatment with an apropriate alcohol or an appropriate amine.

An amino group present can be alkylated as described hereinbefore or can be acylated by treatment with an acid halide or acid anhydride in a manner known per se.

The etherification or esterification of a hydroxy group present can be carried out in a manner known per se; for example, by reaction with an appropriate halide or with an appropriate acid halide or acid anhydride.

The reduction of a carboxyl group can be carried out in a manner known per se; for example, using diborane or lithium aluminium hydride in an inert organic solvent.

The oxidation of an alkylthio group can be carried out in a manner known per se; for example, using hydrogen peroxide.

The compounds of formula I can be converted into acid addition salts, for example, by treatment with an inorganic acid such as a hydrohalic acid (e.g. hydrochloric acid or hydrobromic acid), sulphuric acid, phosphoric acid or the like or with an organic acid such as oxalic acid, tartaric acid, citric acid, methanesulphonic acid or the like. Of the acid addition salts of compounds of formula I, the pharmeceutically acceptable acid addition salts are preferred. If, in the course of the process of this invention, an acid addition salt of a compound of formula I is obtained, then such a salt can be converted into the free base in a known manner (e.g. by treatment with alkali) and the free base can, if desired, be converted into another acid addition salt.

Those compounds of formula I which contain an asymmetric carbon atom can be present in a racemic or optically active form and it will be understood that this invention includes not only the racemic but also the optically active forms. A racemate can, if desired, be resolved into the optical antipodes in a manner known per se; for example, by fractional crystallization of the corresponding salts with an optically active acid.

The compounds of formula I and their acid addition salts possess valuable coronary-dilating properties and can accordingly be used, inter alia, for the treatment of angina pectoris.

The coronary-dilating activity can be measured by the following method:

Mongrels weighing between 20 and 38 kg are used for the tests. The test animals are anaesthetised with ca 30 mg/kg i.v. pentobarbital and the anaesthesia is maintained with chloralose-urethane. The animals are artificially respired with atmospheric air. After opening the thorax, the heart is exposed and a previously calibrated flow-probe of an electromagnetic flowmeter for measuring the blood flow-rate is placed around the ramus circumflexus of the left coronary artery. The arterial blood pressure is measured with a pressure transducer via a catheter in the arteria femoralis. Further, a calibrated extensive measuring strip for the direct measurement of the myocardial contraction force is sutured on to the surface of the left ventricle. The pulse wave of the blood pressure triggers a tachograph for measuring the heart frequency. Water-soluble compounds are administered intravenously dissolved in an isotonic sodium chloride solution, water-insoluble compounds are administered dissolved in propylene glycol or the compounds are administered intraduodenally as a suspension in gum arabic. The maximum activity of a compound is calculated according to each dosage in percent of the starting value and represented graphically. In the measurement of the coronary blood-flow, the duration of activity is also carefully observed.

The results obtained are compiled in the following Table, n denoting the number of animals used.

ble pharmaceutical carrier material. This carrier material may be an organic or inorganic, inert carrier material suitable for enteral or parenteral administration such as, for example, water, gelatine, gum arabic, lactose, starch, magnesium stearate, talc, vegetable oils, polyalkyleneglycols, petroleum jelly etc. The pharmaceutical preparations can be made up in a solid form (e.g. as tablets, dragees or capsules) or in a liquid form (e.g. as solution, suspensions or emulsions). The pharmaceutical preparations may be sterilized and/or may contain adjuvants such as preservatives, stabilizers, wetting agents, emulsifiers, salts for varying the osmotic pressure or buffers.

The daily dose in the case of oral administration lies between about 10 mg and 200 mg. The daily dose in the case of intravenous administration lies between about 1 mg and 20 mg.

The aforementioned dosages are, however, only given by way of example and can be modified according to the particular requirements of the subject and the administering party.

EXAMPLE 1

74.7 g of 3,4-dimethoxybenzaldehyde are dissolved in 1250 ml of chloroform, treated with 50 ml of 1,3-propanedithiol and cooled at 0° C with stirring. 20 ml of boron trifluoride etherate are added and the mixture is left to stand in a refrigerator for 18 hours. The mixture is then washed three times successively with 500 ml of a 7% potassium hydroxide solution and 500 ml of a 10% sodium chloride solution. The organic extracts are combined, dried over magnesium sulphate and evaporated. The residue is recrystallized twice from ether. There are obtained 102.6 g of 2-(3,4-dimethoxyphenyl)-m-dithiane of melting point 99° – 101° C.

The following dithiane can be manufactured in an analogous manner:

2-(o-methoxyphenyl)-m-dithiane of melting point 126°–127° C (from methylene chloride/isopropyl ether);

2-phenyl-m-dithiane of melting point 72°–73° C (from methylene chloride/isopropyl ether);

2-(p-chlorophenyl)-m-dithiane of melting point

Table

| Compound | DL 50 mg/kg p.c. | Coronary flow increase (CF) | | | | n: |
|---|---|---|---|---|---|---|
| | | 1 mg i.v. | | 3 mg i.v. | | |
| | | CF % | Time in minutes | CF % | Time in minutes | |
| N-(3,4-Dimethoxyphenethyl)-2-(3,4-dimethoxyphenyl)-N-methyl-m-dithiane-2-propyl-amine | 250–500 | +138.6 ± 8.4 | 10.4 ± 1.6 | +109 ± 11.8 | 23.4 ± 5.5 | 5 |
| N-(3,4-Dimethoxyphenethyl)-2-(3,4-dimethoxyphenyl)-N-methyl-m-dithiane-2-propyl-amine-1,1,3,3-tetraoxide | 250–500 | +142.6 ± 23.3 | 20.2 ± 3.9 | +230.4 ± 20.9 | 54.0 ± 8.6 | 5 |
| N-(3,4-Dimethoxyphenethyl)-2-(2-naphthyl)-N-methyl-m-dithiane-2-propylamine | 250–500 | +213 | 25 | +194 | 45 | 2 |
| N-(3,4-Dimethoxyphenethyl)-2-(m-nitrophenyl)-N-methyl-m-dithiane-2-propylamine-1,1,3,3-tetraoxide | 500–1000 | +202 | 25 | +170 | 30 | 2 |
| N-(3,4-Dimethoxyphenethyl)-2-(3,4-dimethoxyphenyl)-N-ethyl-m-dithiane-2-propyl-amine-1,1,3,3-tetraoxide | 500–1000 | +197 | 8 | +267 | 15 | 2 |

The compounds of formula I and their pharmaceutically acceptable acid addition salts may be used as medicaments in the form of pharmaceutical preparations which contain them in association with a compati- 87°–88° C (from methylene chloride/isopropyl ether);

2-(m-methoxyphenyl)-m-dithiane of melting point 62°–63° C (from isopropyl ether);

2-(3,4,5-trimethoxyphenyl)-m-dithiane of melting point 88°–89° C (from methylene chlorideisopropyl ether);

2-(m-chlorophenyl)-m-dithiane of melting point 63°–64° C (from cyclohexane);

2-(3,5-dimethoxyphenyl)-m-dithiane of melting point 90°–91° C (from cyclohexane);

p-(m-dithian-2-yl)-N,N-dimethylaniline of melting point 118°–119° C (from cyclohexane);

2-(m-nitrophenyl)-m-dithiane of melting point 117°–118° C (from methylene chloride/methanol);

2-(3,4-methylenedioxyphenyl)-m-dithiane of melting point 86°–97° C (from cyclohexane);

2-p-tolyl-m-dithiane of melting point 89°–90° C (from ether/hexane);

2-(m-bromophenyl)-m-dithiane of melting point 78°–79° C (from cyclohexane);

2-(2-naphthyl)-m-dithiane of melting point 110°–111° C (from cyclohexane);

2-(2,4,5-trimethoxyphenyl)-m-dithiane of melting point 156°–157° C (from methylene chloride/methanol);

2-(p-fluorophenyl)-m-dithiane of melting point 105°–106° C (from cyclohexane);

2-(4-biphenylyl)-m-dithiane of melting point 148°–151° C (from tetrahydrofuran/cyclohexane);

2-($\alpha$, $\alpha$, $\alpha$-trifluoro-p-toyl)-m-dithiane of melting point 103°–104° C (from cyclohexane);

2-(1-naphthyl)-m-dithiane of melting point 147°–148° C (from cyclohexane);

2(3-benzyloxy-4-methoxyphenyl)-m-dithiane of melting point 168°–170° C (from cyclohexane);

2-(4-benzyloxy-3-methoxyphenyl)-m-dithiane of melting point 118°–119° C (from cyclohexane);

2-(2-thienyl)-m-dithiane of melting point 74°–75° C (from cyclohexane); 2-($\alpha$, $\alpha$, $\alpha$-trifluoro-m-tolyl)-m-dithiane of melting point 69°–71° C (from heptane);

2-(p-isopropylphenyl)-m-dithiane of melting point 58°–59° C (from hexane);

2-(3,4-xylyl)-m-dithiane of melting point 74°–75° C (from petroleum ether);

2-(3-butoxy-4-methoxyphenyl)-m-dithiane;

2-(4-ethoxy-3-methoxyphenyl)-m-dithiane of melting point 88°–90° C (from methylene chloride/isopropyl ether);

m-(m-dithian-2-yl)-benzonitrile of melting point 84°–86° C (from isopropyl ether);

6-(m-dithian-2-yl)-1,4-benzodioxan of melting point 140°–142° C (from methylene chloride/isopropyl ether);

2-(4-methoxy-m-toyl)-m-dithiane of melting point 75°–77° C (from cyclohexane).

EXAMPLE 2

60 g of 2-(3,4-dimethoxyphenyl)-m-dithiane(prepared as described in Example 1) are dissolved in 470 ml of glacial acetic acid and treated at room temperature with 235 ml of 30% hydrogen peroxide, the temperature of the solution rising to ca 40° C. The solution is left to stand overnight at room temperature. The solution is then heated for 2 hours at 100° C. After cooling to room temperature, the crystalline precipitate is filtered off under a vacuum, washed with some glacial acetic acid, dried in vacuo at 60° C overnight and then ecrystallized from acetonitrile. There are obtained 57.1 g of 2(3,4-dimethoxyphenyl-m-dithiane-1,1, 3,3-tetraoxide of melting point 243°–245° C.

The following dithiane tetraoxides can be manufactured in an analogous manner:

2-(m-bromophenyl)-m-dithiane-1,1,3,3-tetraoxide of melting point 230°–231° C (from acetonitrile);

2-(p-fluorophenyl-m-dithiane-1,1,3,3-tetraoxide of melting point 283°–284° C (from acetonitrile);

2-(m-nitrophenyl)-m-dithiane-1,1,3,3-tetraoxide of melting point 256°–257° C (from acetonitrile);

2-(3,4,5-trimethoxyphenyl)-m-dithiane-1,1,3,3-tetraoxide of melting point > 310° C (from acetonitrile);

2-(2-naphthyl)-m-dithiane-1,1,3,3-tetraoxide of melting point 277°–278° C (from acetone/acetonitrile);

2-p-tolyl-m-dithiane-1,1,3,3-tetraoxide of melting point 284°–285° C (from acetonitrile);

2-(4-benzyloxy-3-methoxypenyl)-m-dithiane-1,1,3,3-tetraoxide of melting point 220°–223° C (from acetone/acetonitrile);

2-(3,4-dimethoxyphenyl)-1,3-dithiolane-1,1,3,3-tetraoxide of melting point 194°–196° C (from acetone/acetonitrile);

2-(3,4-methylenedioxyphenyl)-m-dithiane-1,1,3,3-tetraoxide of melting point > 300° C (from acetone/acetonitrile);

2-(2'-thienyl)-m-dithiane-1,1,3,3-tetraoxide of melting point 300° C (from acetone/acetonitrile);

2-(3,4-dichlorophenyl)-m-dithiane-1,1,3,3-tetraoxide of melting point 254°–255° C (from glacial acetic acid/water);

2-($\alpha$, $\alpha$, $\alpha$-trifluoro-m-tolyl)-m-dithiane-1,1,3,3-tetraoxide of melting point 239°–242° C (from glacial acetic acid/water);

2-(p-isopropylphenyl-m-dithiane-1,1,3,3-tetraoxide of melting point 204°–205° C (from acetonitrile/ethanol;

2-(3,4-xylyl)-m-dithiane-1,1,3,3-tetraoxide of melting point 268°–269° C (from acetonitrile/methanol);

2-(3-butoxy-4-methoxyphenyl)-m-dithiane-1,1,3,3-tetraoxide of melting point 225°–227° C (from glacial acetic acid/water);

2-(4-ethoxy-3-methoxyphenyl)-m-dithiane-1,1,3,3-tetraoxide of melting point 242°–244° C (from acetone/acetonitrile);

m-(m-dithian-2'-yl)-benzonitrile-1', 1', 3', 3'-tetraoxide of melting point 259°–260° C (from glacial acetic acid/water);

6-(m-dithian-2'-yl)-1,4-benzodioxan-1', 1', 3', 3'-tetraoxide of melting point 232° C (decomposition) (from glacial acetic acid/water);

2-(4-methoxy-m-tolyl)-m-dithiane-1', 1', 3', 3'-tetraoxide of melting point 225°–227° C (from glacial acetic acid/water).

EXAMPLE 3

19.2 g of 2-(3,4-dimethoxyphenyl)-m-dithiane (prepared as described in Example 1) and 200 ml of tetrahydrofuran are cooled to −60° C in a sulphonation flask while gassing with argon and slowly treated with 33 ml of butyl lithium in hexane. The mixture is then stirred at −20° C for 2 hours. A solution of 18 g of N-(3-chloropropyl)-3,4-dimethoxy-N-methyl-phenethylamine in 200 ml of tetrahydrofuran is added dropwise thereto at −70° C within 15 minutes. The mixture is then left to stand for 18 hours at −20° C in a deepfreezer and for 3 hours at room temperature. The solution is then poured on to water and extracted three times with ether. The ethereal extracts three times with 250 ml of 1-N hydrochloric acid. The acidic extracts are treated with 3-N sodium hydroxide up to pH <12 and the separated oil is extracted with ether. The organic extracts are dried over magnesium sulphate and evaporated. The thus obtained oil (30 g) is dissolved in ethyl acetate and treated with ethereal hydrogen bromide. The precipitate which separates is recrystallized from ethanol. There is obtained N-(3,4-dimethoxyphenethyl)-2-(3,4-dimethoxyphenyl)-N-methyl-m-dithiane-2-propylamine hydrobromide of melting point 170°–172° C.

Analysis for $C_{26}H_{37}NO_4S_2 \cdot HBr$
Calculated: C 54.54  H 6.69  N 2.45  Br 13.95
Found:      C 54.54  H 6.74  N 2.31  Br 14.05

The N-(3-chloropropyl)-3,4-dimethoxy-N-methyl-phenethylamine used as the starting material can be prepared as follows:

292.5 g of N-methyl-homoveratrylamine are dissolved in 1000 ml of dimethylformamide and treated with 415 g of anhydrous potassium carbonate. The mixture is stirred at 5° C, treated with 237 g of 1,3-tromochloropropane in 500 ml of dimethylformamide, stirred for a further 4 hours at room temperature and then poured into 5 liters of water. The separated oil is extracted three times with 2 liters of ether each time. The organic extracts are dried with magnesium sulphate and evaporated in vacuo. The residual oil is distilled at between 69° C and 70° C with a mercury diffusion pump at 0.005 Torr. There are obtained 206.7 g of N-(3-chloropropyl)-3,4-dimethyoxy-N-methyl-phenethylamine of boiling point 60°–70° C/0.005 Torr.

The following compounds can be prepared in an analogous manner to that described in this Example:

N-(3,4-dimethoxyphenethyl)-2-(m-methoxyphenyl)-N-methyl-m-dithiane-2-propylamine hydrochloride of melting point 113°–115° C (from acetone);

N-(3,4-dimethoxyphenethyl)-2-(3,4,5-trimethoxyphenyl)-N-methyl-m-dithiane-2-propylamine hydrochloride or melting point 147°–150° C (from acetone);

N-(3,4-dimethoxyphenethyl)-2-(-methoxyphenyl)-N-methyl-m-dithiane-2-propylamine hydrochloride of melting point 160°– ° C (from acetone);

N-(3,4-dimethoxyphenethyl)-2-(o-methoxyphenyl)-N-methyl-m-dithiane-2-propylamine hydrochloride of melting point 151°–152° C (from acetone);

2-(p-chlorophenyl)-N-(3,4-dimethoxyphenethyl)-N-methyl-m-dithiane-2-propylamine hydrochloride of melting point 137°–139° C (from acetone);

N-(3,4-dimethoxyphenethyl)-N-methyl-2-phenyl-m-dithiane-2-propylamine hydrochloride of melting point 170°–172° C (from acetone);

N-(3,4-dimethoxyphenethyl)-N-methyl-2-(3,4-methylenedioxyphenyl-m-dithiane-2-propylamine hydrochloride of melting point 139°–141° C (from acetone);

N-(3,4-dimethyoxyphenethyl)-N-methyl-2-(p-tolyl)-m-dithiane-2-propylamine hydrochloride of melting point 139°–141° C (from acetone);

2-(m-chlorophenyl)-N-(3,4-dimethoxyphenethyl)-N-methyl-m-dithiane-2-propylamine hydrochloride of melting point 108°–110° C (from acetone);

N-(3,4-dimethoxypenethyl)-2-(3,5-dimethylxyphenyl-N-methyl-m-dithiane-2-propylamine oxalate (1:1) of melting point 155°–156° C (from acetone);

N-(3,4-dimethoxyphenethyl)2-(p-dimethylaminophenyl)-N-methyl-m-dithiane-2-propylamine hydrochloride of melting point 183°–184° C (from acetone);

N-(3,4-dimethoxyphenethyl)-N-methyl-2-(2-naphthyl)-m-dithiane-2-propylamine hydrochloride of melting point 195°–196° C (from acetone);

N-(3,4-dimethoxyphenethyl-N-methyl-2-(2,4,5-trimethyoxyphenyl)-m-dithiane-2-propylamine hydrochloride of melting point 156°–158° C (from acetone);

N-(3,4-dimethoxyphenethyl)-2-(p-fluorophenyl)-N-methyl-m-dithiane-2-propylamine hydrochloride of melting point 138°–139° C (from acetone);

2-(4-biphenylyl)-N-(3,4-dimethoxyphenethyl)-N-methyl-m-dithiane-2-propylamine oxalate (1:1) of melting point 167°–169° C (from acetone);

N-(p-chlorophenethyl)-N-methyl-2-phenyl-m-dithiane-2-propylamine hydrochloride of melting point 145°–147° C (from acetone), starting from 2-phenyl-m-dithiane and N-(3-chloropropyl)-4-chloro-N-methyl-phenethylamine;

N-methyl-N-phenethyl-2-phenyl-m-dithiane-2-propylamine hydrochloride of melting point 136°–137° C (from acetone), starting from 2-phenyl-m-dithiane and N-(3-chloropropyl)-N-methyl-phenethylamine (boiling point 78°–80° C/0.001 Torr);

N-(3,4-dimethoxyphenethyl)-N-methyl-2-phenyl-m-dithiane-2-ethylamine hydrochloride of melting point 172°–174° C (from acetone), starting from 2-phenyl-m-dithiane and N-(2-chloroethyl)-3,4-dimethoxy-N-methyl-phenethylamine;

N-(3,4-dimethoxyphenethyl)-N-methyl-2(thienyl)-m-dithiane-2-propylamine hydrochloride of melting point 138°–140° C (from acetone);

rac-N-(3,4-dimethoxyphenethyl)-2-(3,4-dimethoxyphenyl)-N, dimethyl-m-dithiane-2-propylamine oxalate (1:1) of melting point 138°–139° C (from acetone/ethyl acetate), starting from 2-(3,4-dimethoxyphenyl)-m-dithiane and N-(3-chloro-2-methylpropyl)-3,4-dimethoxy-N-methyl-phenethylamine;

2-(3,4-dimethoxyphenyl)-N-[4-(3,4-dimethoxyphenyl)-butyl]N-methyl-m-dithiane-2-propylamine.

EXAMPLE 4

35.2 g of 2-(3,4-dimethoxyphenyl)-m-dithiane-1,1,3,3-tetraoxide (prepared as described in Example 2) are suspended in 180 ml of absolute dioxane and treated with 2.53 g of sodium. The mixture is boiled under argon for 20 hours, the sodium passing completely into solution. 27.2 g of N-(3-chloropropyl)-3,4-dimethoxy-N-methyl-phenethylamine (prepared as described in Example 3) are then added at room temperature, the cloudy solution is stirred at room temperature for 1 hour and boiled at reflux for 3 hours. The mixture is poured on to ice/water and extracted three times with ethyl acetate. The ethyl acetate extracts are combined and extracted three times with 1-N hydrochloric acid. The acidic extracts are made alkaline and extracted three times with chloroform. The chloroform extracts are combined, washed with water, dried over magnesium sulphate and evaporated. The crystalline residue is recrystallized from methanol and there are obtained crystals of melting point 143°–145° C.

For the preparation of the hydrochloride, the base is dissolved in acetone and treated in an ice-bath with 20 ml of hydrogen chloride in dioxane. The crystalline salt is filtered off under a vacuum and recrystallized from acetonitrile/ acetone (1:3). The thus-obtained N-(3,4-dimethoxyphenethyl)-2-(3,4-dimethoxyphenyl)-N- methyl-m-dithiane-2-propylamine-1,1,3,3-tetraoxide hydrochloride is dried overnight in a high vacuum at 120° C. There are obtained 38.9 g of a substance of melting point 167°–169° C.

Analysis:

| Analysis: | | | | | |
|---|---|---|---|---|---|
| Calculated: | C 52.74 | H 6.47 | N 2.36 | Cl 5.99 | S 10.83 |
| Found: | C 52.58 | H 6.58 | N 2.16 | Cl 6.19 | S 10.53 |

The following compounds can be prepared in an analogous manner to that described in this Example:

N-(3,4-dimethoxyphenethyl)-N-methyl-2-(2-naphthyl)-m-dithiane-2-propylamine-1,1,3,3-tetraoxide oxalate (1:1) of melting point 190°–191° C (from acetone/methanol);

N-(3,4-dimethoxyphenethyl)-N-methyl-2-(3,4,5-trimethoxyphenyl)-m-dithiane-2-propylamine-1,1,3,3-tetraoxide oxalate (1:1) of melting point 146°–148° C (from acetone/ethyl acetate);

2-(m-bromophenyl)-N-(3,4-dimethoxyphenethyl)-N-methyl-m-dithiane-2-propylamine-1,1,3,3-tetraoxide hydrochloride of melting point 158°–160° C (from methanolic hydrogen chloride/ethyl acetate);

2-(m-nitrophenyl)-N-(3,4-dimethoxyphenethyl)-N-methyl-m-dithiane-2-propylamine-1,1,3,3-tetraoxide hydrochloride of melting point 212°–214° C (from acetone);

N-(3,4-dimethoxyphenethyl)-2-(p-fluorophenyl)-N-methyl-m-dithiane-2-propylamine-1,1,3,3-tetraoxide hydrochloride of melting point 234°–236° C (from methanol);

N-(3,4-dimethoxyphenethyl)-N-methyl-2-phenyl-m-dithiane-2-propylamine-1,1,3,3-tetraoxide hydrochloride of melting point 149° C (decomposition) (from methanol);

N-(3,4-dimethoxyphenethyl)-2-(3,4-dimethoxyphenyl)-N-ethyl-m-dithiane-2-propylamine-1,1,3,3-tetraoxide oxalate (1:1) of melting point 177°–179° C (from methanol/acetone) [from 2-(3,4-dimethoxyphenyl)-m-dithiane-1,1,3,3-tetraoxide and N-(3-chlorophenyl)-3-chloropropyl)-3,4-dimethoxy-N-ethylphenethylamine];

N-(3,4-dimethoxyphenethyl)-2-(4-isopropylphenyl)-N-methyl-m-dithiane-20propylamine-1,1,3,3-tetraoxide hydrochloride of melting point 225°–227° C (from hydrogen chloride in dioxane/ethyl acetate);

N-(3,4-dimethoxyphenethyl)-2-(3-trifluoromethylphenyl)-N-methyl-m-dithiane-2-propylamine-1,1,3,3-tetraoxide oxalate of melting point 128°–130° C (from acetone);

N,2-bis(3,4-dimethoxyphenyl)-N-methyl-m-dithiane-2-propylamine-1,1,3,3-tetraoxide;

2-(3,4-dimethoxyphenyl)-N-[4-(3,4-dimethoxyphenyl)-butyl]-m-dithiane-2-propylamine-1,1,3,3-tetraoxide;

N-(3,4-dimethoxyphenethyl)-N-methyl-2-(3,4-xylyl)-m-dithiane-2-propylamine-1,1,3,3-tetraoxide hydrochloride of melting point 176°–178° C (from acetonitrile);

2-(3-butoxy-4-methoxyphenyl)-N-(3,4-dimethoxyphenethyl)-N-methyl-m-dithiane-2-propylamine-1,1,3,3-tetraoxide of melting point 84°–85° C (from methanol/isopropyl ether);

N-[3-[2'-(3,4-dimethoxyphenyl)-m-dithian-2'-yl]-propyl]-N-methyl-1,4-benzodioxan-6-ethylamine-1',1',31'3'-tetraoxide hydrochloride of melting point 208°–210° C (from acetonitrile);

N-[4-(3,4-dimethoxyphenyl)-butyl]-2-(p-isopropylphenyl)-N-methyl-m-dithiane-2-propylamine-1,1,3,3-tetraoxide hydrochloride of melting point 148°-150° C (from ethyl acetate/hydrogen chloride in dioxane);

rac-2-(3,4-dimethoxyphenyl)-N-[3-(3,4-dimethoxyphenyl)-1-methylpropyl]-N-methyl-m-dithiane-2-propylamine-1,1,3,3-tetraoxide of melting point 115°–117° C;

N-(3,4-dimethoxyphenethyl)-2-(4-ethoxy-3-methoxyphenyl)-N-methyl-m-dithiane-2-propylamine-1,1,3,3-tetraoxide hydrochloride of melting point 190°–192° C (from acetonitrile);

m-{2' -[3-[(3,4-dimethoxyphenethyl-methylamino]-propyl]-m-dithian-2'-yl}-benzonitrile-1', 1', 3', 3'-tetraoxide hydrochloride of melting point 160° C (decomposition);

2-(1,4-benzodioxan-6-yl)-N-(3,4-dimethoxyphenethyl)-N-methyl-m-dithiane-2-propylamine-1,1,3,3-tetraoxide hydrochloride of melting point 201°–204° C;

N-(3,4-dimethoxyphenethyl)-2-(4-methoxy-m-tolyl)-N-methyl-m-dithiane-2-propylamine-1,1,3,3-tetraoxide hydrochloride of melting point 146° C (decomposition) (from acetone);

m- 2'[3-[4-(3,4-dimethoxyphenyl)-butyl]-methylaminopropyl]-m-dithian-2'-yl},-benzonitrile-1',1',3',3'-tetraoxide hydrochloride of melting point 121°–122° C (from water);

2-(3,4-dimethoxyphenyl)-N-methyl-N-(p-methylphenethyl)-m-dithiane-2-propylamine-1,1,3,3-tetraoxide hydrochloride of melting point 169°–171° C (from acetone/ethyl acetate).

EXAMPLE 5

6.08 g of 2-(3,4-methylenedioxyphenyl)-m-dithiane-1,1,3,3-tetraoxide (prepared as described in Example 2) are stirred under argon with 25 ml of absolute dimethylformamide and treated with 0.8 of a 55% sodium hydride suspension. The mixture is left to react for 0.5 hour at room temperature and for 1 hours at 40° C. After cooling to room temperature, 4.8 g of N-(3-chloropropyl)-3,4-dimethoxy-N-methyl-phenethylamine (prepared as described in Example 3) are added and the mixture is heated at 100° C for 16 hours. The cooled mixture is then poured on to ice and extracted three times with ethyl acetate. The organic extracts are washed with water, dried over magnesium sulphate and evaporated in vacuo. The residual oil is dissolved in acetone and treated with 5 ml of a 6-N hydrogen chloride solution in dioxane. The precipitate, which is filtered off under a vacuum, is recrystallized from acetone. There are obtained 7.5 g of N-3,4-dimethoxyphenethyl)-N-methyl-2-(3,4-methylenedioxyphenyl)-m-dithiane-2-propylamine-1,1,3,3-tetraoxide hydrochloride of melting point 247°–248° C.

Analysis:

| Analysis: | | | |
|---|---|---|---|
| Calculated: | C 52.12 | H 5.95 | N 2.43 |
| Found: | C 51.91 | H 5.86 | N 2.23 |

The following compounds can be prepared in a manner analogous to that described in this Example:

N-(3,4-dimethoxyphenethyl)-N-methyl-2-p-tolyl-m-dithiane-2-propylamine-1,1,3,3-tetraoxide hydrochloride of melting point 203°-207° C (from acetonitrile-/acetone);

2-(4-benzyloxy)-3-methoxyphenyl-N-(3,4-dimethoxyphenethyl)-N-methyl-m-dithiane-2-propylamine-1,1,3,3-tetraoxide hydrochloride of melting point 220°-221° C (from ethanol);

N-(3,4-dimethoxyphenethyl)-N-methyl-2-(2'-thienyl)-m-dithiane-2-propylamine-1,1,3,3,-tetraoxide hydrochloride of melting point 179°-182° C (from acetone);

2-(3,4-dichlorophenyl)-N-(3,4-dimethoxyphenethyl)-N-methyl-m-dithiane-2-propylamine-1,1,3,3-tetraoxide hydrochloride of melting point 175°-177° C (from methanol);

N-(3,4-dimethoxyphenethyl)-2-(3,4-dimethoxyphenyl)-N-methyl-m-dithiane-2-ethylamine-1,1,3,3-tetraoxide oxalate (1:1) of melting point 202°-204° C (from acetone).

EXAMPLE 6

10 g of 3', 4'-dimethoxy-4-(methylveratrylamino)-butyrophenone hydrochloride are dissolved in 50 ml of chloroform and treated with 3.25 g of 1,3-propanedithiol. Hydrogen chloride is conducted into the mixture at room temperature. After standing for 24 hours, the mixture is poured on to water, made basic with 3-N sodium hydroxide and extracted with ether. After drying and evaporation of the solvent, the oily residue is dissolved in acetone and treated with an equivalent amount of anhydrous oxalic acid. The crystalline precipitate is recrystallized from acetone. There is obtained 2-(3,4-dimethoxyphenyl)-N-methyl-N-veratryl-m-dithiane-2-propylamine oxalate (1:1) of melting point 133°-136° C.

Analysis:

| Analysis: | | | |
|---|---|---|---|
| Calculated: | C 57.12 | H 6.57 | N 2.47 |
| Found: | C 56.88 | H 6.64 | N 2.46 |

The 3',4',-dimethoxy-4-(methylveratrylamino)-butyrophenone used as the starting material can be prepared as follows:

500 g of polyphosphoric acid and 69 g of veratrol are added to a 1 liter round-bottomed flask. To this are added 61 g of 4-chlorobutyric acid in one portion, the temperature rising steadily to 55° C. After 1 hours, the entire mixture is poured on to ice. The mixture is then extracted with a mixture of ether/methylene chloride (3:1). The organic extracts are extracted with water, then with a saturated sodium bicarbonate solution and finally again with water, dried over magnesium sulphate and evaporated in vacuo. The residual crystal mass is recrystallized from ether. There are obtained 62.9 g of 3,4-dimethoxy-γ-chlorobutyrophenone of melting point 91°-92° C.

12 g of 3,4-dimethoxy-γ-chlorobutyrophenone are treated with 40 ml of N-ethyl-N,N-diisopropylamine and 9 g of N-methyl-homoveratrylamine and stirred at 120° C for 6 hours. After evaporation of the solvent in vacuo, the viscous mass is treated with ether and sodium hydroxide. The organic extracts are washed with water and extracted with 1-N hydrochloric acid. The acidic extracts are then made alkaline and extracted with ether. The ether extracts are combined, dried over sodium sulphate and evaporated. The thus-obtained 3',4'-dimethoxy-4-(methylveratrylamino)-butyrophenone, which is pure according to thin-layer chromatography, can be used without further purification.

The following compounds can be prepared in a manner analogous to that described in this Example:

N-(3,4-dimethoxyphenethyl)-2-(3,4-dimethoxyphenyl)-N-methyl-m-dithiane-2-butylamine oxalate (1:1) of melting point 134°-136° C (from acetone);

starting from 1,3-propanedithiol and 5-[3,4-dimethoxyphenethyl)-methylamino]-3',4'-dimethoxyvalerophenone (melting point of the hydrochloride 165°-166° C), obtained from 3,4-dimethoxy-δ-chlorovalerophenone and N-methyl-homoveratrylamine.

N-(3,4-Dimethoxyphenethyl)-2-(3,4-dimethoxyphenyl)-N-methyl-m-dithiane-2-pentylamine oxalate (1:1) of melting point 109°-111° C (from acetone);

starting from 1,3-propanedithiol and 6-[(3,4-dimethoxyphenethyl)-methylamino]-3',4'-dimethoxyhexanophenone (melting point of the hydrochloride 128°-129° C), obtained from 6-chloro-3',4'-dimethoxyhexanophenone and N-methyl-homoveratrylamine.

2-(3,4-Dimethoxyphenyl)-N-[3,4-dimethoxyphenyl)-propyl]-N-methyl-m-dithiane-2-propylamine oxalate (1:1) of melting point 116°-118° C (from acetone);

starting from 1,3-propanedithiol and 3',4'-dimethoxy-4-[[(3,4-dimethoxyphenyl)-propyl]-methylamino]-butyrophenone, obtained from 3,4-dimethoxy-γ-chlorobutyrophenone and 3-(3,4-dimethoxyphenyl)-N-methylpropylamine.

2-(3,4-Dimethoxyphenyl)-N-methyl-N-(α-methylphenethyl)-m-dithiane-2-propylamine oxalate (1:1) of melting point 131°-132° C (from acetone-/ethyl acetate);

starting from 1,3-propanedithiol and 4-[(3,4-dimethoxy-α-methylphenethyl)-methylamino]-3',4'-dimethoxybutyrophenone, obtained from 3,4-dimethoxy- -chlorobutyrophenone and N, α-dimethyl-β-phenylethylamine (boiling point 130°-140° C/20 mm Hg).

N-3,4-Dimethoxyphenethyl)-2-(3,4-dimethoxyphenyl)-N-methyl-1,3-dithiolane-2-propylamine oxalate (1:1) of melting point 150°-152° C (from acetone);

starting from

4-[(3,4-dimethoxyphenethyl)-methylamino]-3',4'-dimethoxybutyrophenone and 1,2-ethanedithiol.

EXAMPLE 7

10.4 g of 2-(3-chloropropyl)-2-(3,4-dimethoxyphenyl)-m-dithiane-1,1,3,3-tetraoxide are treated with 5.11 g of N-methyl-homoveratrylamine, 30 ml of N-ethyl-N,N-diisopropylamine and 70 ml of dimethylformamide. The solution is heated at 120° C for 6 hours. After evaporation, the residue is worked-up in a manner analogous to that described in Example 5. There is obtained N-(3,4-dimethoxyphenethyl)-2-(3,4-dimethoxyphenyl(-N-methyl-m-dithiane-2-propylamine-1,1,3,3-tetraoxide hydrochloride of melting point 167°–169° C.

The following compounds can be prepared in a manner analogous to the foregoing:

N-(3,4-dimethoxyphenethyl)-N-methyl-2-phenyl-m-dithiane-2-propylamine-1,1,3,3-tetraoxide hydrochloride of melting point 149° C (decomposition) (from methanol);

N-(p-chlorophenethyl)-N-methyl-2-phenyl-m-dithiane-2-propylamine-1,1,3,3-tetraoxide hydrochloride of melting point 246°–249° C (decomposition) (from methanol/methylene chloride);

N-methyl-N-phenethyl-2-phenyl-m-dithiane-2-propylamine-1,1,3,3-tetraoxide hydrochloride of melting point 165°–167° C (from acetone);

2-(3,4-dimethoxyphenyl)-N-methyl-N-veratryl-m-dithiane-2-propylamine-1,1,3,3-tetraoxide of melting point 137°–139° C (from acetone/ethanol);

N-(3,4-dimethoxyphenethyl)-2-(3,4-dimethoxyphenyl)-m-dithiane-2-propylamine-1,1,3,3-tetraoxide hydrochloride of melting point 130°–132° C (from acetone).

The 2-(3-chloropropyl)-2-(3,4-dimethoxyphenyl)-m-dithiane-1,1,3,3-tetraoxide used as a standing material in this Example can be prepared as follows:

10.9 g of 3,4-dimethoxy- γ -chlorobutyrophenone (prepared as described in Example 6) are dissolved in 120 ml of chloroform and treated with 5 ml of 1,3-propanedithiol and 1 ml of boron trifluoride etherate at room temperature. After 1 hour at room temperature, the chloroform solution is washed three times with water, three times with 1-N sodium hydroxide and again three times with water. The organic phases are dried over magnesium sulphate and evaporated in vacuo. The oily residue is immediately dissolved in 500 ml of chloroform at 0°–5° C and treated with 45.7 g of solid m-chloroperbenzoic acid in such a manner that the temperature does not exceed 5° C. The mixture is subsequently left in a refrigerator for 64 hours. The organic phase is washed three times with 1-N sodium hydroxide and three times with water, dried over magnesium sulphate and evaporated in vacuo. The residue is recyrstallized from methylene chloride/isopropyl ether. There is obtained 2-(3-chloropropyl)-2-(3,4-dimethoxyphenyl)-m-dithiane-1,1,3,3-tetraoxide of melting point 183°–184° C.

The 2-(3-chloropropyl)-2-phenyl-m-dithiane-1,1,3,3-tetraoxide also used as a starting material in this Example can be prepared as follows:

19.63 g of 2-phenyl-m-dithiane are dissolved in 300 ml of tetrahydrofuran 43.5 ml of a solution of butyl lithium in hexane are slowly added dropwise at −70° C while gassing with argon. The mixture is stirred for a total of 1.5 hours at −20° C. The red solution obtained is added to a solution of 15.74 g of 1,3-bromochloropropane in 250 ml of absolute tetrahydrofuran at −70° C. The thus-obtained solution is left to stand for 1 hour at −20° C and for 1 hour at room temperature. The solvent is evaporated in vacuo and the oily residue taken up in ether. The ethereal phase is washed with 1-N sodium hydroxide and with water, dried over magnesium sulphate and evaporated in vacuo. The thus-obtained 2-(3-chloropropyl)-2-phenyl-m-dithiane is peroxidized at 0°–5° C with m-chloroperbenzoic acid in chloroform as described in the previous paragraph. After recrystallized from ethyl acetate, there is obtained 2-(3-chloropropyl)-2-phenyl-m-dithiane-1,1,3,3-tetraoxide of melting point 182° C.

EXAMPLE 8

3.76 g of 2-(3,4-dimethoxyphenyl)-2-(2,3-epoxypropyl)-m-dithiane-1,1,3,3-tetraoxide are heated at reflux for 18 hours under argon with 50 ml of ethanol, 30 ml of chloroform and 1.95 g of N-methyl-homoveratrylamine. After evaporation of the solvent, the residue is chromatographed on silica gel with chloroform/ethanol (98:2). The oil obtained is dissolved in acetone and treated with an equivalent amount of anhydrous oxalic acid. The precipitate is filtered off and recrystallized from methanol/acetone. The racemic α -[(3,4-dimethoxyphenethyl)-methylamino]-methyl-2-(3,4-dimethoxyphenyl)-m-dithiane-2-ethanol-1,1,3,3-tetraoxide oxalate (1:1) obtained crystallizes with 1 mol of acetone and melts at 162°–164° C.

Analysis:

| Analysis: | | | |
|---|---|---|---|
| Calculated: | C 51.73 | H 6.30 | N 1.95 |
| Found: | C 51.68 | H 6.53 | N 2.00 |

The 2-(3,4-dimethoxyphenyl)-2-(2,3-epoxypropyl)-m-dithiane-1,1,3,3-tetraoxide used as the starting material can be prepared as follows:

9.6 of 2-(3,4-dimethoxyphenyl)-m-dithiane-1,1,3,3-tetraoxide (prepared as described in Example 2) are dissolved in 35 ml of dimethylformamide and, with stirring under argon, treated with 1.2 g of sodium hydride at room temperature. The suspension is stirred at 40° C for a further 0.5 hour, then cooled and treated with 2.8 g of epichlorohydrin. The mixture is then heated at 100° C for 16 hours. After cooling to room temperature, the suspension is poured on to water and the oily material extracted with chloroform. After evaporation of the solvent, the residue is chromatographed on silica gel with chloroform/ethanol (98:2). The 2-(3,4-dimethoxyphenyl)-2-(2,3-epoxypropyl)-m-dithiane-1,1,3,3-tetraoxide obtained is recrystallized from methylene chloride/ethanol and has a melting point of 175°–176° C.

EXAMPLE 9

3.65 g of 2-(3-chloropropyl)-2-(3,4-dimethoxyphenyl)-m-dithiane-1,3-dioxide, 7.8 g of N-methyl-homoveratrylamine and 20 ml of dimethyl sulphoxide are heated at 50° C under argon for 16 hours. The solution is then poured into 200 ml of water and made strongly alkaline. The excess N-methyl-homoveratrylamine is extracted with ether. The alkaline solution is then extracted with methylene chloride. The methylene chloride extracts are dried over magnesium sulphate. After evaporation of the solvent, the residue is taken up in acetone and treated with hydrogen chloride in dioxane (up to pH 2). The crystalline residue is recrystallized from acetone/acetonitrile and there is obtained N-(3,4-dimethoxyphenethyl)-2-(3,4-dimethoxyphenyl)-N-methyl-m-dithiane-2-propylamine-1,3-dioxide hydrochloride of melting point 148°–149° C (diastereomeric mixture). The 2-(3-chloropropyl)-2-(3,4-dimethoxyphenyl)-m-dithiane-1,3-dioxide used as the starting material can be prepared as follows:

76.9 g of 2-(3,4-dimethoxyphenyl)-m-dithiane (prepared as described in Example 1) are dissolved in 900 ml of absolute tetrahydrofuran, the solution is cooled to −70° C and treated with 128 ml of a butyl lithium solution in such a manner that the temperature does not exceed −60° C. The mixture is then held for 2 hours at −20° C, a precipitate forming. The mixture is again cooled to −70° C and 47.3 g of 1,3-bromochloropropane in 750 ml of absolute tetrahydrofuran are added. The mixture is then held for 1 hour at −20° C and for 1 hour at room temperature. The tetrahydrofuran is then evaporated, the residue taken up in ether and extracted. After evaporation of the solvent, there is obtained 2-(3-chloropropyl)-2-(3,4-dimethoxyphenyl)-m-dithiane.

55.25 g of 2-(3-chloropropyl)-2-(3,4-dimethoxyphenyl)-m-dithiane are dissolved in 500 ml of glacial acetic acid. While stirring at 5° C, a solution of 34 g of 30% hydrogen peroxide in 300 ml of glacial acetic acid is added thereto within 2 hours. The mixture is then left to stand for 60 hours at room temperature and then concentrated in vacuo at 40° C. The oil obtained is chromatographed on 1.5 kg of silica gel with chloroform/ethanol, initially 98:2 and then 95:5. After recrystallization from acetonitrile, there is obtained 2-(3-chloropropyl)-2-(3,4-dimethoxyphenyl)-m-dithiane-1,3-dioxide of melting point 163°–164° C (diasteromeric mixture).

EXAMPLE 10

In a manner analogous to that described in Example 8, but starting from 2-(3,4-dimethoxyphenyl)-2-(2,3-epoxypropyl)-m-dithiane and N-methyl-homoveratrylamine, there can be prepared racemic α-[(3,4-dimethoxyphenthyl)-methylamino]-methyl-2-(3,4-dimethoxyphenyl)-m-dithiane-2-ethanol. The hydrobromide of this compound crystallizes from acetonitrile/ethyl acetate and melts at 97°–99° C.

The 2-(3,4-dimethoxyphenyl)-2-(2,3-epoxypropyl)-m-dithiane used as the starting material can be prepared in a manner analogous to that described in Example 9 starting from 2-(3,4-dimethoxyphenyl)-m-dithiane (prepared as described in Example 1) using epichlorohydrin instead of 1,3-bromochloropropane.

EXAMPLE 11

3.4 g of lithium aluminium hydride in 60 ml of tetrahydrofuran are heated to reflux. 14.7 g of N-(3,4-dimethylphenethyl)-2-(3,4-dimethoxyphenyl)-m-dithiane-2-propionamide in 80 ml of tetrahydrofuran are than added dropwise. The suspension obtained is heated at reflux for a further 3 hours, then cooled to 0° C and carefully treated with 50 ml of a saturated sodium sulphate solution. The mixture is then filtered off under a vacuum, the solution diluted with water and extracted with ether. The ethereal extracts are washed with 1-N sodium hydroxide, then with water, dried over magnesium sulphate and evaporated. The oily residue is chromatographed on silica gel using chloroform/ethanol (95:5). The base obtained is dissolved in acetone and treated with an equivalent amount of anhydrous oxalic acid. The resulting precipitate is recrystallized from methanol/acetone. The thus-obtained N-(3,4-dimethoxyphenethyl)-2-(3,4-dimethoxyphenyl)-m-dithiane-2-propylamine oxalate (1:1) melts at 186°–188° C.

Analysis:

| Analysis: | | | |
|---|---|---|---|
| Calculated: | C 57.12 | H 6.57 | N 2.67 |
| Found: | C 56.97 | H 6.73 | N 2.39 |

The N-(3,4-dimethoxyphenethyl)-2-(3,4-dimethoxyphenyl)-m-dithiane-2-propionamide used as the starting material can be prepared as follows:

50 g of 3-veratroylpropionic acid in 400 ml of chloroform and 22.7 g of 1,3-propanedithiol are treated with hydrogen chloride up to saturation while stirring. After 3 hours at room temperature, the solution is evaporated to 50 ml and diluted with ether. The resulting solution is extracted three times with 5% sodium carbonate. The basic phases are combined and made acidic with concentrated hydrochloric acid. The precipitated product is extracted with ether/methylene chloride (1:3). The organic extracts are dried and evaporated. The residue is recrystallized from ethanol, there being obtained 2-(3,4-dimethoxyphenyl)-m-dithiane-2-propionic acid of melting point 134°–135° C.

13.2 g of 2-(3,4-dimethoxyphenyl)-m-dithiane-2-proprionic acid, 4 g of triethylamine and 180 ml of tetrahydrofuran are cooled to 0° C and treated dropwise within 10 minutes with 5.44 g of chloroformic acid isobutyl ester in 80 ml of tetrahydrofuran. The mixture is then held at room temperature for 3 hours and treated at 0° C with 7.25 g of homoveratrylamine in 40 ml of tetrahydrofuran. The suspension is left to stand at 3° C for 48 hours, then evaporated, treated with water and extracted with ether/methylene chloride (3:1). The ethereal extracts are washed with water, sodium bicarbonate solution, 1-N tartaric acid and water. The organic phase is dried over magnesium sulphate and evaporated. The residue is crystallized from methylene chloride/ether at 0° C. There is obtained N-(3,4-dimethoxyphenethyl)-2-(3,4-dimethoxyphenyl)-m-dithiane-2-propionamide of melting point 135°–136° C.

N-(3,4-Dimethoxyphenethyl)-2-(3,4-dimethoxyphenyl)-N-methyl-m-dithiane-2-propylamine hydrobromide can be manufactured in a manner analogous to that described in the foregoing; melting point 170°–172° C (from ethanol).

EXAMPLE 12

0.5 g of 2-{[3-[2''-(3,4-dimethoxyphenyl)-m-dithian-2''-yl]-propyl]-methylamino}-3', 4'-dimethoxyacetophenone-1'', 1'', 3'', 3''-tetraoxide is dissolved in 15 ml of ethanol and 30 ml of tetrahydrofuran and treated with 50 g of sodium borohydride. After stirring for 16 hours, the mixture is treated with 15 ml of 1-N hydrochloric acid and then with 12 ml of 1-N sodium hydroxide solution. The tetrahydrofuran is removed by evaporation and the residue extracted with methylene chloride. The organic extracts are washed with water, dried over magnesium sulphate and evaporated in a vacuum. The crystals obtained are recrystallized from methanol and there is obtained 0.3 g of α-/{[3-[2'-(3,4-dimethoxyphenyl)-m-dithian-2'-yl]-propyl] -methylamino}-methyl/-veratrylalcohol-1', 1', 3', 3'-tetraoxide of melting point 132°–133° C.

The 2-{[3-[2''-(3,4-dimethoxyphenyl)-m-dithian-2''-yl[-propyl] - methylamino}-3', 4'-dimethoxyacetophenone-1'', 1'', 3'', 3''-tetraoxide used as the starting material can be prepared by reacting 2-(3-chloropropyl)-2-(3,4-dimethoxyphenyl)-m-dithiane-1,1,3,3-tetraoxide with ω-methylamino-3,4-dimethoxyacetophenone; melting point 140° C (decomposition) (from acetone).

EXAMPLE 13

10 g of N-(3,4-dimethoxyphenethyl)-2-(3,4-dimethoxyphenyl)-N-methyl-m-dithiane-2-pentylamine (prepared as described in Example 6) are dissolved in 50 ml of glacial acetic acid and treated at room temperature with 20 ml of 30% hydrogen peroxide. After 3 hours, the mixture is heated at 35° C for 3 hours and then at 40° C for 18 hours. The solution is then poured onto water, made basic with sodium hydroxide and extracted with methylene chloride. After removal of the solvent, the residue is chromatographed on silica gel using a mixture of chloroform, methanol and saturated ammonia (97:3). The product obtained is dissolved in acetone and treated with an equivalent amount of oxalic acid. The resulting precipitate is recrystallized from acetone/methanol. There is obtained N-(3,4-dimethoxyphenethyl)-2-(3,4-dimethoxyphenyl)-N-methyl-m-dithiane-2-pentylamine-1,1,3,3-tetraoxide oxalate (1:1) of melting point 189°–191° C.
Analysis:

| Analysis: | | | |
|---|---|---|---|
| Calculated: | C 53.48 | H 6.43 | N 2.08 |
| Found: | C 53.37 | H 6.50 | N 1.87 |

The following compounds can be manufactured in a manner analogous to that described in the foregoing:

N-(3,4-Dimethoxyphenethyl)-2-(3,4-dimethoxyphenyl)-N-methyl-m-dithiane-2-butylamine-1,1,3,3-tetraoxide oxalate of melting point 161°–163° C (from acetone/methanol), (base: 123°–126° C from ethanol), starting from
   N-(3,4-dimethoxyphenethyl)-2-(2,4-dimethoxyphenyl)-N-methyl-m-dithiane-2-butylamine (prepared as described in Example 6).
2-(3,4-Dimethoxyphenyl)-N-[3-(3,4-dimethoxyphenyl)-propyl]-N-methyl-m-dithiane-2-propylamine-1,1,3,3-tetraoxide hydrobromide of melting point 138°–140° C (from acetonitrile/ethyl acetate), starting from
   2-(3,4-dimethoxyphenyl)-N-[3-(3,4-dimethoxyphenyl)-propyl]-N-methyl-m-dithiane-2-propylamine (prepared as described in Example 6).
Racemic N-(3,4-Dimethoxyphenethyl)-2-(3,4-dimethoxyphenyl)-N,-dimethyl-m-dithiane-2-propylamine-1,1,3,3-tetraoxide hydrochloride of melting point 183°–185° C (from acetone/ethyl acetate), starting from
   racemic N-(3,4-dimethoxyphenethyl)-2-(3,4-dimethoxyphenyl)-N,β-dimethyl-m-dithiane-2-propylamine (prepared as described in Example 3).
2-(3,4-Dimethoxyphenyl)-N-methyl-N-methyl(-phenethyl)-m-dithane-2-propylamine-1,1,3,3-tetraoxide hydrochloride of melting point 185°–187° C (from acetone/ethyl acetate), starting from
   2-(3,4-dimethoxyphenyl)-N-methyl-N-(α-methylphenethyl)-m-dithiane-2-propylamine (prepared as described in Example 6).

EXAMPLE 14

11.2 g of 2-(4-benzyloxy-3-methoxyphenyl)-N-(3,4-dimethoxyphenethyl)-N-methyl-m-dithiane-2-propylamine-1,1,3,3-tetraoxide(prepared as described in Example 5) are heated with 100 ml of 48% hydrobromic acid for 2 minutes on a steam bath. The aqueous solution is then extracted with ether, evaporated in vacuo and azeotropically distilled three times with ethanol-benzene. The residue is crystallized from acetone. The thus-obtained crystalline mass is recrystallized three times from methanol/acetonitrile and there is obtained 4-{2'-[3-[(3,4-dimethoxyphenethyl)-methylamino]-propyl]-m-dithian-2'-yl}-2-methoxyphenol-1', 1', 3', 3'-tetraoxide hydrobromide of melting point 192° C (decomposition).
Analysis for $C_{25}H_{35}NO_8S_2 \cdot HBr$

| Analysis for $C_{25}H_{35}NO_8S_2 \cdot HBr$ | | | |
|---|---|---|---|
| Calculated: | C 48.23 | H 5.83 | N 2.25 |
| Found: | C 48.12 | H 5.93 | N 2.07 |

In an analogous manner starting from 2-(3-benzyloxy-3-methoxyphenyl)-N-(3,4-dimethoxyphenethyl)-N-methyl-m-dithiane-2-propylamine-1,1,3,3-tetraoxide there can be obtained 5-{2'-[3-[(3,4-dimethoxyphenethyl)-methylamino]-propyl]-m-dithian-2'-yl}-2-methoxyphenol-1', 1', 3', 3'-tetraoxide hydrobromide of melting point 201° C (decomposition) (from acetonitrile).

EXAMPLE 15

2 g of 5-{2'-[3-(3,4-dimethoxyphenethyl)-methylaminopropyl]-m-dithian-2'-yl}-2-methoxyphenol-1', 1', 3', 3'-tetraoxide are dissolved in absolute pyridine and treated with an excess of acetic anhydride. After leaving for 16 hours at room temperature, the solvent is removed by evaporation and the residue chromatographed on silica gel. The 5-{2'-[3-(3,4-dimethoxyphenethyl)-methylamInopropyl]-m-dithian-2'-yl}-2-methoxyphenyl acetate 1', 1', 3', 3'-tetraoxide is obtained as a thick oil.
Analysis:

| Analysis: | | | |
|---|---|---|---|
| Calculated: | C 55.67 | H 6.39 | N 2.40 |
| Found: | C 55.22 | H 6.41 | N 2.23 |

EXAMPLE 16

0.3 g of 2-(3,4-dimethoxyphenyl)-N-methyl-m-dithiane-2-propylamine-1,1, 3,3-tetraoxide are treated with 0.16 g of 3,4-dimethoxy-β-phenethyl chloride, 5 ml of N,N-diisopropyl-N-ethylamine and 1.5 ml of dimethylformamide and the mixture is heated at 130° C for 16 hours. The solution is then partitioned between water and ethyl acetate. The residue is chromatographed on silica gel and there is obtained N-(3,4-dimethoxyphenethyl)-2-(3,4-dimethoxyphenyl)-N-methyl-m-dithiane-2-propylamine-1,1,3,3-tetraoxide of melting point 144° C (from methanol).

The 2-(3,4-dimethoxyphenyl)-N-methyl-m-dithiane-2-propylamine-1,1,3,3-tetraoxide used as the starting material can be prepared as follows:

3.95 g of 2-(3-chloropropyl)-2-(3,4-dimethoxyphenyl)-m-dithiane-1,1,3,3-tetraoxide are dissolved in 50 ml of dimethylformamide. The solution is cooled to 0° C and treated with 15 g of methylamine. The mixture is heated at 40° C under pressure for 18 hours. The solution is then concentrated and the crystalline residue recrystallized from a small amount of methanol.

There is thus obtained the desired starting material of melting point 164° C.

EXAMPLE 17

1 g of N-(3,4-dimethoxyphenethyl)-2-(3,4-dimethoxyphenyl)-m-dithiane-2-propylamine is dissolved in 20 ml of absolute pyridine and treated with 200 ml of acetic anhydride. After 18 hours, the mixture is concentrated and the residue partitioned between ether and sodium carbonate (5%). After evaporation of the solvent, there are obtained 1.2 g of an oil which is dissolved in 20 ml of absolute tetrahydrofuran. This solution is slowly added dropwise to a suspension of 0.4 g of lithium aluminium hydride and 20 ml of absolute tetrahydrofuran. The mixture is slowly treated with a concentrated aqueous sodium sulphate solution and then filtered under suction. After evaporation of the solvent, the residue is partitioned between ether and water and the organic extracts are worked-up. The oily residue is treated with oxalic acid in acetone/ethyl acetate, there crystallizing out N-(3,4-dimethoxyphenethyl)-2-(3,4-dimethoxyphenyl)-N-ethyl-m-dithiane-2-propylamine-1,1,3,3-tetraoxide oxalate of melting point 126°-127° C.

EXAMPLE 18

1 g of homoveratric acid is dissolved in 15 ml of absolute tetrahydrofuran and treated wih 0.15 g of triethylamine. 0.72 g of chloroformic acid isobutyl ester are then slowly added dropwise at 0°-5° C and the mixture is stirred for 1 hour at 5°-10° C. There is then added dropwise a solution of 1.63 g of 2-(3,4-dimethoxyphenyl)-N-methyl-m-dithiane-2-propylamine [prepared in a manner analogous to that described in Example 15 from 2-(γ-chloropropyl)-2-(3,4-dimethoxyphenyl)-m-dithiane and methylamine] in 5 ml of tetrahydrofuran. The resulting mixture is left to stand at room temperature overnight. After evaporation of the solvent, the residue is partitioned between 1-M hydrochloric acid and ether. The organic extracts are washed with 5% sodium carbonate solution and water. After drying over magnesium sulphate, the solvent is removed by evaporation. The oily residue (1.5g) is dissolved in 15 ml of tetrahydrofuran and added dropwise to a suspension of 0.15 g of lithium aluminium hydride under reflux and under argon. The mixture is boiled for 2 hours and then treated slowly with a concentrated sodium sulphate solution in water and then with 10 ml of methylene chloride. The mixture is filtered under suction and then concentrated. The residue is chromatographed on silica gel and there is obtained N-(3,4-dimethoxyphenethyl)-2-(3,4-dimethoxyphenyl)-N-methyl-m-dithiane-2-propylamine in the form of a thick oil.

The following Examples illustrate typical pharmaceutical preparations containing the sulphur-containing derivatives provided by the present invention:

EXAMPLE A

Capsules containing the following ingredients are prepared in the usual manner:

| | |
|---|---|
| N-(3,4-dimethoxyphenethyl)-2-(3,4-dimethoxyphenyl)-N-methyl-m-dithiane-2-propylamine | 25 mg |
| Mannitol | 115 mg |
| Maize starch | 40 mg |
| Talc | 18 mg |
| Magnesium stearate | 2 mg |

EXAMPLE B

Tablets containing the following ingredients are prepared in the usual manner:

| | |
|---|---|
| N-(3,4-dimethoxyphenethyl)-2-(3,4-dimethoxyphenyl)-N-methyl-m-dithiane-2-propylamine-1,1,3,3-tetraoxide | 25 mg |
| Lactose | 90 mg |
| Maize starch | 75 mg |
| Magnesium stearate | 1 mg |
| Talc | 9 mg |
| | 200 mg |

What we claim is:
1. A compound of the formula

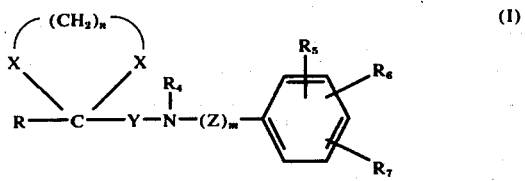

, wherein R is a group of the formula

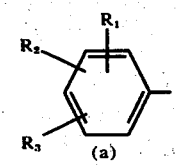

in which $R_1$, $R_2$ and $R_3$ each independently is hydrogen, halogen, lower alkyl, lower alkoxy, aryl-(lower alkoxy), aryloxy, phenyl, nitro, amino, lower alkylthio, trifluoromethyl, hydroxy, cyano, di(lower alkyl)amino, lower alkanoylamino, carboxyl, lower alkoxycarbonyl, lower alkylsulphonyl, hydroxymethyl, lower alkanoyloxy, amido, lower alkanoyl, sulphamoyl, mono(lower alkyl)-sulphamoyl, di(lower alkyl) sulphamoyl, aminocarbonyloxy, mono(lower alkyl)-amino-carbonyloxy, di(lower alkyl)aminocarbonyloxy or (lower alkylamino)-(lower alkyl) in which "aryl" means unsubstituted or substituted phenyl. The substituent being selected from halogen, lower alkyl, lower alkoxy, nitro and amino; $R_4$ is hydrogen or lower alkyl; $R_5$, $R_6$ and $R_7$ each independently is hydrogen, halogen, lower alkyl, lower alkoxy, hydroxy or benzyloxy; X is a sulphur atom, SO or $SO_2$; Y is a straight-chain or branched-chain, aliphatic group which may be substituted with hydroxy and containing 2-8 carbon atoms, of which 2-4 carbon atoms are present in the chain; and Z is a straight-chain or branched-chain aliphatic group which may be substituted with hydroxy and containing 1-8 carbon atoms, of which 1-4 carbon atoms are present in the chain;

$m$ is zero or 1 and $n$ is 2 or 3, and acid addition salts thereof.

2. The compound of claim 1, wherein one of the symbols $R_1$, $R_2$ and $R_3$ is hydrogen and the other symbols each indepenently is lower alkoxy.

3. The compound of claim 2 wherein two of the symbols $R_1$, $R_2$ and $R_3$ are methoxy.

4. The compound of claim 1 wherein one of the symbols $R_5$, $R_6$ and $R_7$ is hydrogen and the other symbols each independently is lower alkoxy.

5. The compound of claim 4, wherein said lower alkoxy group is methoxy.

6. The compound of claim 1, wherein X is a sulphur atom or $SO_2$ and $n$ is 3.

7. The compound of claim 1, wherein Y is the group —$(CH_2)_3$—.

8. The compound of claim 1, wherein $(Z)_m$ is the group —$(CH_2\text{-}CH_2)_m$— in which $m$ is zero or 1.

9. The compound of claim 1, wherein $R_4$ is methyl.

10. The compound of claim 1 of the formula

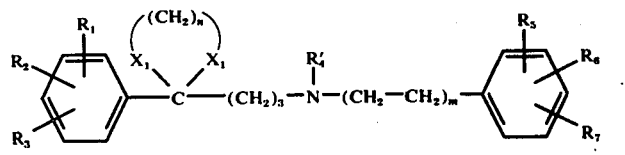

(Ia)

, wherein $R_1$–$R_7$ and $m$ are as in claim 1; $R'_4$ is methyl or ethyl; $X_1$ is a sulphur atom or $SO_2$ and $n$ is 3.

11. The compound of claim 10, wherein one of the symbols $R_1$, $R_2$, and $R_3$ is hydrogen and the other symbols each independently is lower alkoxy.

12. The compound of claim 10, wherein two of the symbols $R_1$, $R_2$ and $R_3$ each is methoxy.

13. The compound of claim 10, wherein one of the symbols $R_5$, $R_6$ and $R_7$ is hydrogen and the other symbols each is lower alkoxy.

14. The compound of claim 13, wherein said lower alkoxy is methoxy.

15. The compound of claim 14 which is N-(3,4-dimethoxyphenethyl)-2-(3,4-dimethoxyphenyl)-N-methyl-m-dithiane-2-propylamine-1,1,3,3-tetraoxide.

* * * * *